(12) United States Patent
Durell

(10) Patent No.: US 7,175,593 B2
(45) Date of Patent: *Feb. 13, 2007

(54) VARIABLE VIEW ARTHROSCOPE WITH CHARGE COUPLED DEVICE

(75) Inventor: William E. Durell, North Barrington, IL (US)

(73) Assignee: Durell & Gitelis, Inc., Las Vegas, NV (US)

( * ) Notice: Subject to any disclaimer, the term of this patent is extended or adjusted under 35 U.S.C. 154(b) by 523 days.

This patent is subject to a terminal disclaimer.

(21) Appl. No.: 10/694,446

(22) Filed: Oct. 27, 2003

(65) Prior Publication Data

US 2006/0129032 A1 Jun. 15, 2006

Related U.S. Application Data

(63) Continuation-in-part of application No. 09/650,621, filed on Aug. 30, 2000, now Pat. No. 6,638,216.

(51) Int. Cl.
*A61B 1/00* (2006.01)
(52) U.S. Cl. .................. 600/173; 600/130; 600/176
(58) Field of Classification Search ............. 600/173, 600/176, 130, 131, 106, 107; 385/119; 433/30; 348/65
See application file for complete search history.

(56) References Cited

U.S. PATENT DOCUMENTS

| 1,726,268 | A | 8/1929 | Jahr |
| 2,932,294 | A | 4/1960 | Fourestier et al. |
| 2,987,960 | A | 6/1961 | Sheldon |
| 3,357,433 | A | 12/1967 | Fourestier et al. |
| 3,643,654 | A | 2/1972 | Felbarg |
| 3,856,000 | A | 12/1974 | Chikama |

(Continued)

FOREIGN PATENT DOCUMENTS

WO    WO 95/25460    9/1995

(Continued)

*Primary Examiner*—John P Leubecker
(74) *Attorney, Agent, or Firm*—Wilmer Cutler Pickering Hale and Dorr LLP

(57) ABSTRACT

A variable view arthroscope includes a tubular housing having a longitudinal axis and an input end, an input lens and a CCD in the input end of the housing for capturing and relaying an image object. In some embodiments, a variable view arthroscope with a plurality of viewing positions in a viewing range between a first end viewing position and a second end viewing position includes a tubular housing having a longitudinal axis and an input end, an input lens and a mirror in the housing for obtaining an image object, and a prism, a focusing lens, and a CCD in the housing for capturing and relaying the image object. The input lens and mirror are movable around an axis for varying the view of the arthroscope. In certain embodiments, the tubular housing has a longitudinal axis and an input end and the input lens and CCD are mounted in an input lens holder in the input end of the housing. The input lens and the CCD are movable for varying the view of the arthroscope. The CCD converts the object image into a digital image that can be viewed, for example, on a TV or CRT screen. The CCD can be used to replace a field and relay system, or additional focusing lenses and mirrors, thereby decreasing the cost and complexity of a variable view arthroscope.

19 Claims, 3 Drawing Sheets

U.S. PATENT DOCUMENTS

| | | |
|---|---|---|
| 3,880,148 A | 4/1975 | Kanehira et al. |
| 3,901,220 A | 8/1975 | Koyasu et al. |
| 3,918,438 A | 11/1975 | Hayamizu et al. |
| 4,140,364 A | 2/1979 | Yamashita et al. |
| 4,191,468 A | 3/1980 | Scully |
| 4,640,577 A | 2/1987 | Tsuno |
| 4,697,577 A | 10/1987 | Forkner |
| 4,723,843 A | 2/1988 | Zobel |
| 4,838,247 A | 6/1989 | Forkner |
| 4,846,154 A | 7/1989 | MacAnally et al. |
| 4,858,002 A | 8/1989 | Zobel |
| 4,877,314 A | 10/1989 | Kanamori |
| 5,184,602 A | 2/1993 | Anapliotis et al. |
| 5,424,877 A | 6/1995 | Tsuyuki et al. |
| 5,603,687 A | 2/1997 | Hori et al. |
| 5,613,936 A | 3/1997 | Czarnek et al. |
| 5,643,176 A | 7/1997 | Persidsky |
| 5,743,846 A | 4/1998 | Takahashi et al. |
| 5,876,325 A * | 3/1999 | Mizuno et al. ............. 600/102 |
| 6,110,105 A | 8/2000 | Durell |
| 6,139,490 A | 10/2000 | Breidenthal et al. |
| 6,364,830 B1 | 4/2002 | Durell |
| 6,371,909 B1 | 4/2002 | Hoeg et al. |
| 6,398,725 B1 | 6/2002 | Thompson |
| 6,638,216 B1 | 10/2003 | Durell |
| 2004/0236183 A1 | 11/2004 | Durell |

FOREIGN PATENT DOCUMENTS

| | | |
|---|---|---|
| WO | WO 99/42028 | 8/1999 |
| WO | WO 01/39657 | 6/2001 |

* cited by examiner

VARIABLE VIEW ARTHROSCOPE WITH CHARGE COUPLED DEVICE

RELATED APPLICATIONS

This application is a continuation-in-part of U.S. application Ser. No. 09/650,621, entitled "Variable View Arthroscope," filed Aug. 30, 2000, and invented by William E. Durell now U.S. Pat. No. 6,638,216, which is incorporated herein by this reference.

FIELD OF INVENTION

The invention relates generally to variable view arthroscopes, endoscopes, and similar optical instruments, and more specifically, to variable view arthroscopes using charge-coupled devices (CCDs).

BACKGROUND OF THE INVENTION

Arthroscopes and other similar optical instruments, such as endoscopes, are used in medical applications, such as surgery and examination, as well as in non-medical applications. Although embodiments of the present invention are described in the present application in the context of surgical arthroscopes, embodiments of the present invention may be useful for other applications and the present invention is intended to embrace all suitable variations.

Over the last fifteen or more years, the nature of surgery has changed substantially, with minimally invasive surgery becoming a standard of care. Within the orthopedic field, in particular, arthroscopy and similar techniques have become the most common surgical procedures. Surgery using such techniques is less painful for the patient and, in most instances, can be performed more quickly and safely than with techniques that require greater invasion of the patient's body. Furthermore, the anesthesia associated with arthroscopy and similar procedures is less complicated, more cost effective and can be handled on an outpatient basis. Patients return to normal life more quickly, and hospital stays may be reduced in length or even eliminated. However, all of these benefits are available only if minimally invasive surgery allows for better diagnostic capabilities, improved surgical techniques, and reduced iatrogenic damage.

One drawback of these minimally invasive techniques derives from the technical limitations of the arthroscopes, endoscopes and other principal optical instruments employed. In particular, one significant limitation is the limited field of view afforded by even the best commercially available instruments; in some respects these instruments and techniques have not changed significantly since the 1980s. Improvements in the field of view provided by an arthroscope or like instrument can improve the utility of such devices.

Several techniques for widening the view offered by arthroscopic/endoscopic instruments have been proposed. Generally, such proposals have entailed the packing of a plurality of movable lenses or prisms into the input end of the instrument, posing numerous design challenges and often resulting in various problems, such as precision of construction, precision of relative movements, space requirements, optical distortions, and elimination of undesired "ambient" light.

There is a need for an improved arthroscope that affords the user a broadened effective field of view and that does not require movement of the entire arthroscope to vary its scope of view. There is also a need for an arthroscope with an improved design for object capture and relay. In this specification and in the appended claims, the term "arthroscope" means and should be interpreted to include an endoscope or any other like optical instrument, whether used for surgery or otherwise.

SUMMARY OF INVENTION

The present invention is directed to a variable view arthroscope with a plurality of viewing positions in a viewing range between a first end viewing position and a second end viewing position. In certain embodiments, a variable view arthroscope includes a tubular housing having a longitudinal axis and an input end, an input lens and a mirror in the housing for obtaining an image object, and a prism, a focusing lens, and a CCD in the housing for capturing and relaying the image object. The input lens and mirror are movable around an axis for varying the view of the arthroscope.

In some embodiments, a variable view arthroscope includes a tubular housing having a longitudinal axis and an input end, an input lens and a CCD in the housing for capturing and relaying the image object. In certain embodiments, the tubular housing has a longitudinal axis and an input end and the input lens and CCD are mounted in an input lens holder in the input end of the housing. The input lens and the CCD are movable for varying the view of the arthroscope.

The CCD converts the object image into a digital image that can be viewed, for example, on a TV or CRT screen. The CCD can be used to replace a field and relay system, or additional focusing lenses and mirrors, thereby decreasing the cost and complexity of a variable view arthroscope. Various mechanisms can be provided for moving the optical elements, including the CCD in some embodiments, to vary the view of the arthroscope.

BRIEF DESCRIPTION OF THE DRAWINGS

For a fuller understanding of the present invention, references should be made to the following detailed description taken in connection with the accompanying drawings, not drawn to scale, in which the same reference numerals indicate the same or similar parts, wherein.

DETAILED DESCRIPTION OF THE ILLUSTRATED EMBODIMENTS

Figure 1:
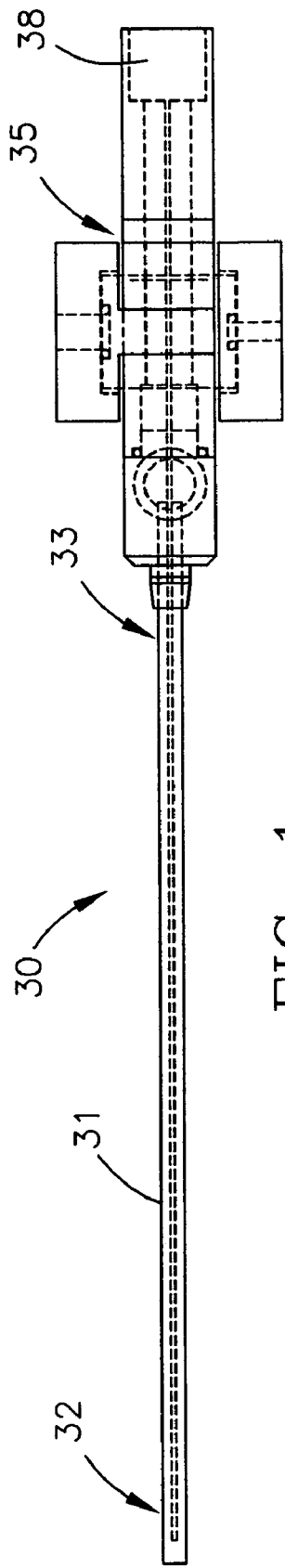
FIG. 1 is a plan view of a variable view arthroscope constructed in accordance with an embodiment of the present invention.
Figure 2:
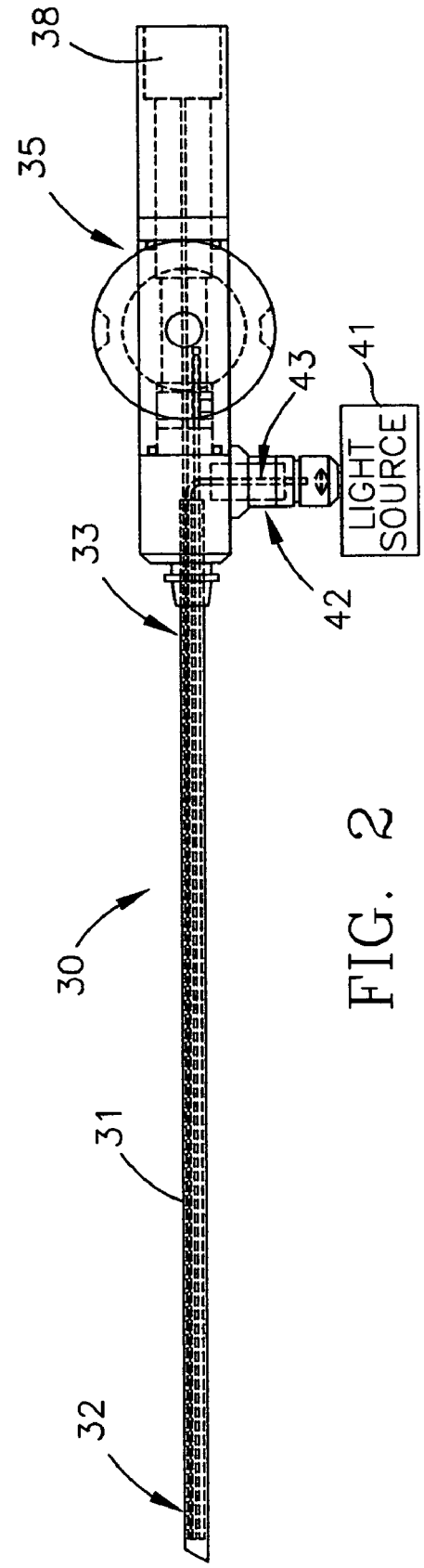
FIG. 2 is a sectional elevation view of the variable view arthroscope of FIG. 1.

A variable view arthroscope in which various embodiments of the present invention can be incorporated is shown in FIGS. 1 and 2. Although shown and described herein as an arthroscope providing up-down view variability, an arthroscope having a similar configuration could be oriented so as to provide a side-to-side view variability or view variability along any other axis. As discussed herein, the object is formed of object rays that include an axial ray at the optical center of the object rim rays at the outer edges or rims of the object image. A variable view arthroscope, generally indicated at 30, includes an elongated housing tube 31, with an object input end 32, and a control end 33, that extends along a central longitudinal axis. Arthroscope 30 includes an outer control portion 35. Housing tube 31, and more specifically its control end 33, may extend into the outer control portion 35 of arthroscope 30. Generally, an object is captured at object input end 32 of housing tube 31, relayed to control end 33, and recorded and displayed from devices connected to socket 38 of arthroscope 30. In some embodiments, socket 38 can be a standard autoclavable medical-type electrical connector with pins that are gold or are gold-plated to prevent corrosion during sterilization and are hermetically sealed in control end 33 of arthroscope 30.

Control end 33 connects to an outer control portion 35 that may include a control, such as a slide, for adjusting the view of arthroscope 30, and a focusing lens assembly (not shown) for adjusting the focus of arthroscope 30. Focusing lens assembly may include, for example, a focusing lens, a zoom lens, and their controls. Focusing lens assembly focuses the object rays onto a CCD located in the input end 32 of arthroscope 30. In certain embodiments, outer control portion 35 of arthroscope 30 also includes a portion of a lighting assembly 42, formed from a light source 41 that is connected to a light relay assembly 43. Lighting assembly 42 illuminates a viewing area beyond object input end 32 of housing tube 31. In the illustrated embodiment, the viewing area is an area in front of object input end 32 of the arthroscope, from about 15 degrees below the longitudinal axis of the arthroscope tube 31 to about 105 degrees above the longitudinal axis of arthroscope tube 31.

Figure 3:
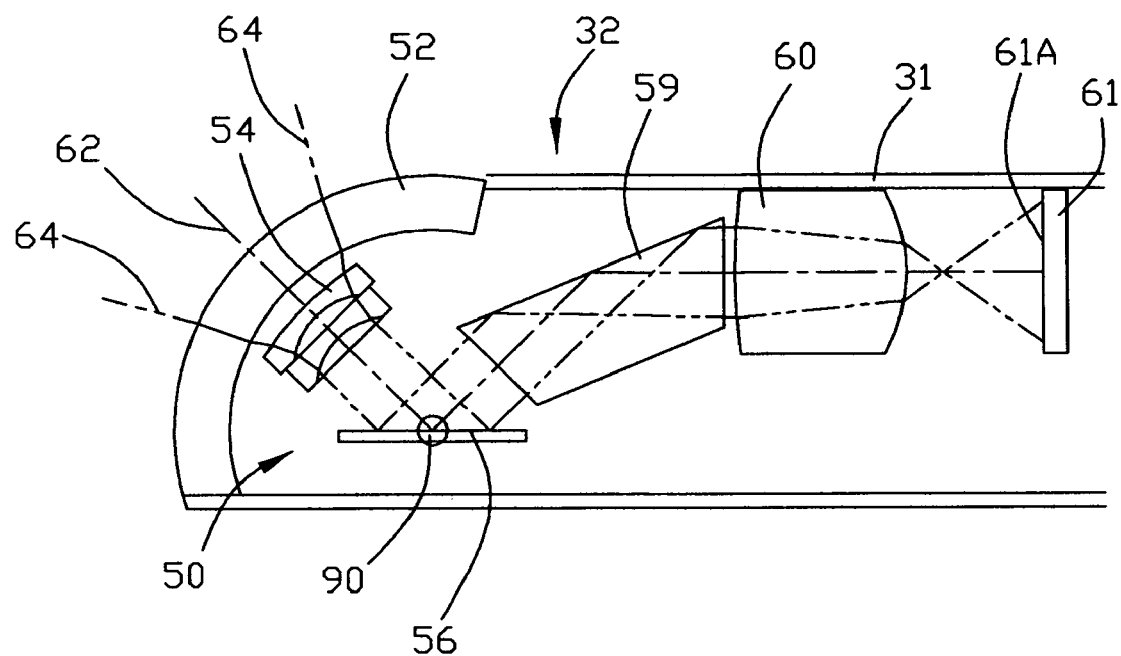
FIG. 3 is a sectional elevation view of the object input end of the arthroscope of FIG. 1, showing portions of an object input assembly constructed in accordance with an embodiment of the present invention, adjust for a middle view.
Figure 4:
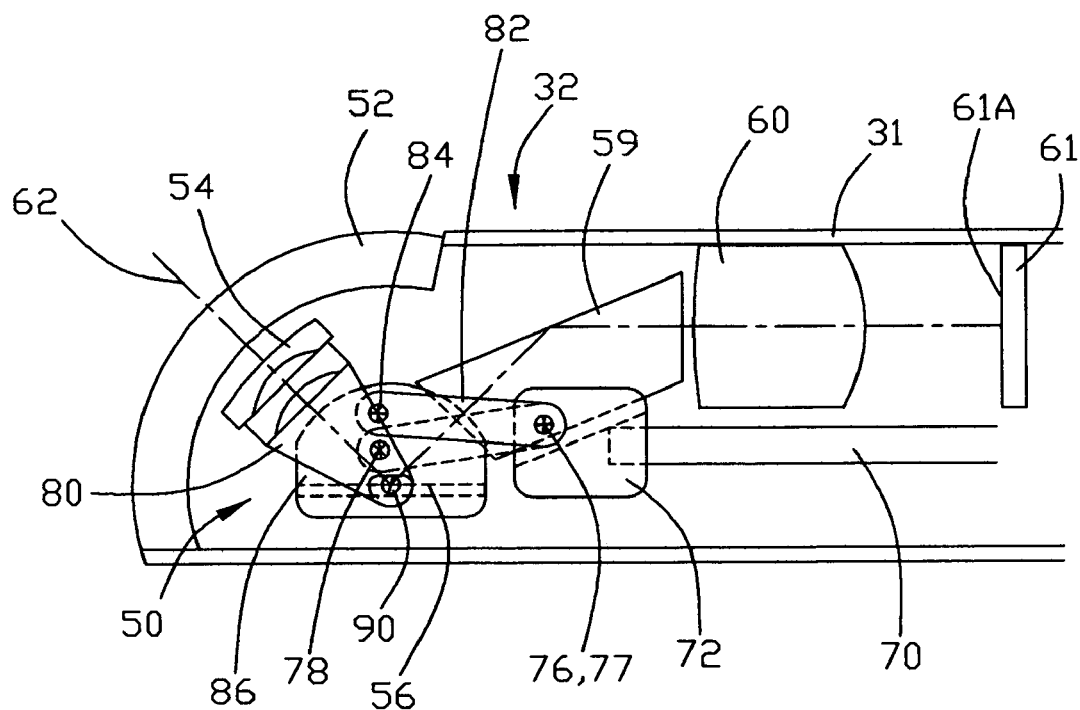
FIG. 4 is a sectional elevation view of the object input end of the arthroscope of FIG. 3, adjusted for a middle view, showing the input lens control and the mirror control, constructed in accordance with an embodiment of the present invention.

Referring now to FIGS. 3 and 4, object input end 32 includes an object input assembly 50. Object input assembly 50 includes an input window 52, an input lens 54, a first mirror 56, a focusing lens 60, a prism 59 and a CCD 61. Input end 32 of housing tube 31 is preferably beveled and closed by input window 52. Input window 52 is preferably a concentric spherical meniscus lens and formed so that the curvatures of the outer and inner surfaces are concentric to each other around a common centerpoint. Input window 52 may be formed of glass or some other suitable material. Input window 52 is fixed in place, such as by adhesive, and also may be sealed to form a sealed closure for the end of housing tube 31. Preferably, input end 32 of housing tube 31 is formed so that the edges of housing tube 31 have a shape similar to the profile shape of input window 52 and extend beyond the surface of input window 52 to afford the greatest protection to input window 52 without interfering with the input object rays during operation of arthroscope 30.

The centerpoint of input window 52 is preferably on the centerline of an axle 90, which is on the front reflecting surface of first mirror 56, and is also preferably on the optical axis of input lens 54. If the centerpoint of input window 52 is positioned on the input lens optical axis, a constant relationship is maintained between the refractive angles of the input object rays as input lens 54 moves from position to position. As a result, the refraction of the input object rays through input window 52 is constant with respect to input lens 54 and distortions are reduced. The dimensions of input window 52 preferably are selected to maximize the range of view of arthroscope 30 in cooperation with the other elements of the object input assembly.

Both input lens 54 and first mirror 56 are movable within housing tube 31 and cooperatively function as a means to vary the view of arthroscope 30 and direct the captured object rays to prism 59. Axle 90 around which both input lens 54 and first mirror 56 move defines a preferred alignment of input lens 54 and first mirror 56. Input lens 54 of object input assembly 50 is positioned inside input end 32 of housing tube 31 and is proximate to input window 52. Although shown as doublet of two spherical lenses in the embodiments illustrated in FIGS. 3 and 4, input lens 54 can consist of any suitable lens. Input lens 54 rotates between a maximum upward view position and a maximum downward view position, approximately corresponding to and limited by the field of view afforded by input window 52. FIGS. 3 and 4 illustrate object input assembly 50 in the middle position of this range of viewing positions. In the illustrated embodiment, input lens 54 is fixedly mounted on an input lens frame 80. Input lens frame 80 is a swing arm that pivots around an axle. Input lens frame 80 supports input lens 54 at one end and pivots around axle 90 at the other end and is moved by a control mechanism. Input lens 54 is mounted on input lens frame 80 such that the optical centerline or axis of input lens 54 is aligned with the centerline of axle 90.

First mirror 56 is accordingly positioned to reflect the object rays received from input lens 54 to prism 59, which is fixed. First mirror 56 pivots around axle 90, in a motion complementary to that of input lens 54. The centerline of axle 90 is coplanar with the front reflecting surface of first mirror 56. As input lens 54 moves, the position of the first mirror must change to preserve the desired orientation of the object rays. Due to the geometry of mirrors, the angle change in a ray reflected from a mirror will be double the angle change in the reflecting plane of the mirror, such as when the mirror rotates from a first position to a second position. Consequently, first mirror 56 rotates around axle 90 at half the rate of angular change at which input lens 54 rotates around axle 90. Therefore, as input lens 54 rotates around axle 90 through a first angle of rotation, first mirror 56 pivots around axle 90 through a second angle of rotation that is half the first angle of rotation.

First mirror 56 correspondingly rotates between a maximum upward view position and a maximum downward view position. With the movement of input lens 54, the rotation of first mirror 56 varies the view of arthroscope 30. In alternative embodiments, input lens 54 and first mirror 56 may be moved between a series of pre-defined positions or may be moved to any position within the range of arthroscope 30. In the illustrated embodiment, first mirror 56 is preferably mounted on a first mirror frame 86 and a control is used to adjust the position of first mirror 56. In the illustrated embodiment, in the middle view of object input assembly 50, the reflecting surface of first mirror 56 is horizontal with respect to longitudinal orientation of tube 31 and input lens 54 is positioned such that the optical axis of input lens 54 is at an angle 45 degrees up from the plane of mirror 56. As shown in FIGS. 3 and 4, for example, the center of the middle view is 45 degrees up from the horizontal, i.e., the longitudinal axis of tube 31.

The object rays obtained through input lens 54, first mirror 56, and prism 59, are preferably relayed to outer control portion 35 of the arthroscope 30 via the focusing lens 60 and CCD 61. CCD 61 may replace, for example, a relay lens assembly. It is preferred that the rays are relayed in a manner that preserves the quality of the image and minimizes aberrations. Prism 59 is preferably fixed to reflect the captured object rays into focusing lens 60 in a direction parallel to the optical axis of focusing lens 60. The optical axis of focusing lens 60 is, in turn, preferably parallel to the longitudinal axis of housing tube 31. Focusing lens 60 is preferably coaxial with the axial ray reflected from prism 59. CCD 61 has a receptor face 61A which captures object rays that impinge upon it. CCD 61 is located on the image plane of focusing lens 60 such that the object rays are focused on receptor face 61A of CCD 61. From CCD 61, the captured image is then relayed to control end 33 for display. Because input lens 54 and mirror 56 are provided in front of CCD 61 and are both movable in coordination, a focused image is maintained on CCD 61 through the total viewing range defined by the maximum upward and maximum downward position.

In alternate embodiments of the invention, a second mirror can be used interchangeably for prism 59. In certain embodiments, the use of prism 59 rather than a second mirror allows for a reduction in the input lens system focal length and improves image quality. In obtaining a CCD image, the object rays pass from the viewing area into input window 52 and through input lens 54, and are reflected from first mirror 56 to prism 59.

The movement of input lens 54 and first mirror 56 allows the viewing position of arthroscope 30 and thus the particular object captured in arthroscope 30 to be variable. The control that adjusts input lens 54 and first mirror 56 adjusts them congruently to maintain the desired alignment. In the illustrated embodiment, a push rod 70 directs the motion of input lens 54 and first mirror 56. The position of input lens 54 is adjusted by push rod 70 engaging input lens frame 80 through an input lens connecting rod 74. Input lens connecting rod 74 is connected to input lens frame 80 through an input lens frame pin 78. As push rod 70 moves back and forth along the longitudinal axis of housing tube 30, connecting rod 74 shifts the position of input lens frame 80, and hence, of the input lens 54. The position of first mirror 56 is adjusted by push rod 70 engaging first mirror frame 86 through a first mirror connecting rod 82. First mirror connecting rod 82 is connected to push rod 70 at push rod yoke 72 by yoke pin 77. Yoke pins 76 and 77 are disposed on opposite sides of push rod yoke 72 and are coaxial. First mirror connecting rod 82 is connected to first mirror frame 86 through a first mirror frame pin 84. As push rod 70 moves back and forth, first mirror connecting rod 82 adjusts the angle of first mirror 56.

In this embodiment, first mirror connecting rod 82 is fastened to the push rod yoke 72 at yoke pin 77 and the input lens connecting rod 74 is connected to the yoke at yoke pin 76. Yoke pins 77 and 76 are coaxial and connecting rods 74, 82 move synchronously. Preferably, the distance from axle 90 to the input lens frame pin 78 is one half the distance from axle 90 to the first mirror frame pin 84. As the radius of the input lens arc is half of the radius of the first mirror, the angular change of input lens 54 is preferably twice the angular change of first mirror 56. Push rod 70 may be operated by any suitable mechanism such as a slide driven by a cam-axle assembly connected to a rotating control knob for the user. The illustrated positioning and relative proportions of the connecting rods 74, 82, axle 90, input lens frame pin 78, and first mirror frame pin 84 preferably minimize any error in the relative angular changes. It should be understood that any mechanical arrangement that preserves the desired geometries of the mirror(s), prism(s), and the input lens(es) is suitable; for example, more than one push rod may be used to implement an effective control.

To minimize distortion in the recorded image, preferably, the object ray path lengths remain constant as the view of the arthroscope varies. The object axial ray 62 passes through the optical center of input lens 54 to the center of first mirror 56. This distance is fixed because the center of first mirror 56 is fixed on the centerline of axle 90 around which input lens 54 rotates with a constant radius. Object axial ray 62 then reflects from the center of first mirror 56 to prism 59, which is fixed with respect to first mirror 56. The axial ray then reflects from prism 59 along the optical axis of focusing lens 60. From focusing lens 60, the object axial ray passes to the CCD. As each segment of object axial ray 62 has a fixed length, the length of object axial ray 62 from input lens 54 to focusing lens 60 remains constant as the view of arthroscope 30 varies. Object rim rays 64 pass through input lens 54 to first mirror 56. As axial ray 62 is coaxial with the optical axis of input lens 54, all object rim rays 64 are symmetric about axial ray 62. As long as all object rays are reflected or refracted symmetrically to any plane normal to axial ray 62, such as the first lens of focusing lens 60, the length of the object rays remain constant. In some embodiments of the present invention, this feature may allow the view to change without changes in distortion and image quality.

Figure 5:
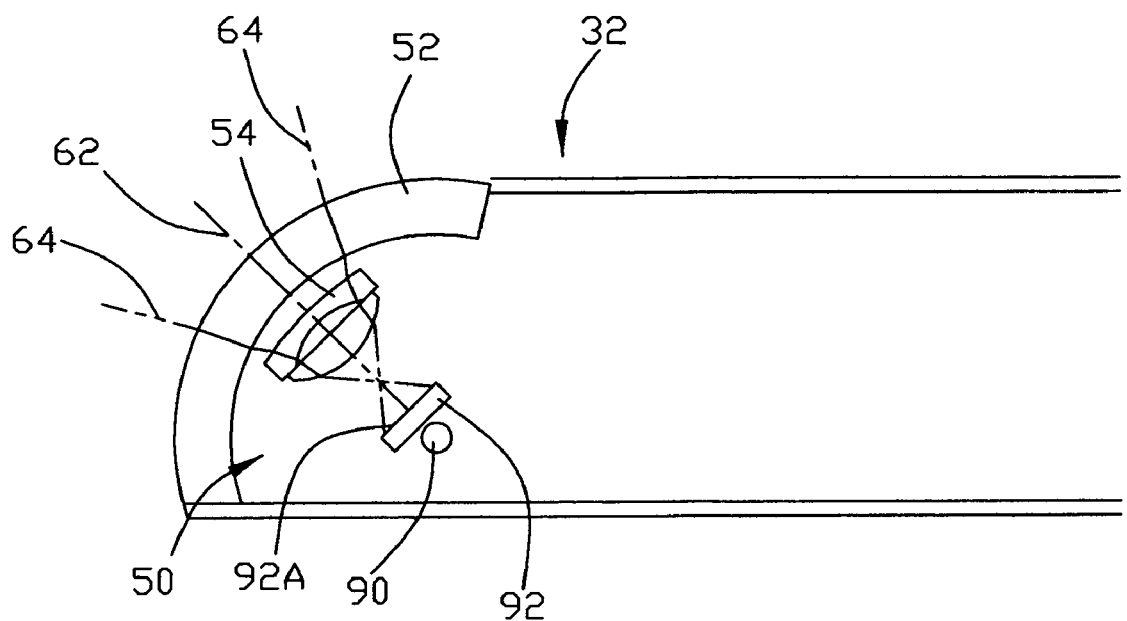
FIG. 5 is an alternate sectional elevation view of the object input end of the arthroscope of FIG. 1, showing portions of an object input assembly constructed in accordance with an alternative embodiment of the present invention, adjusted for a middle view.
Figure 6:
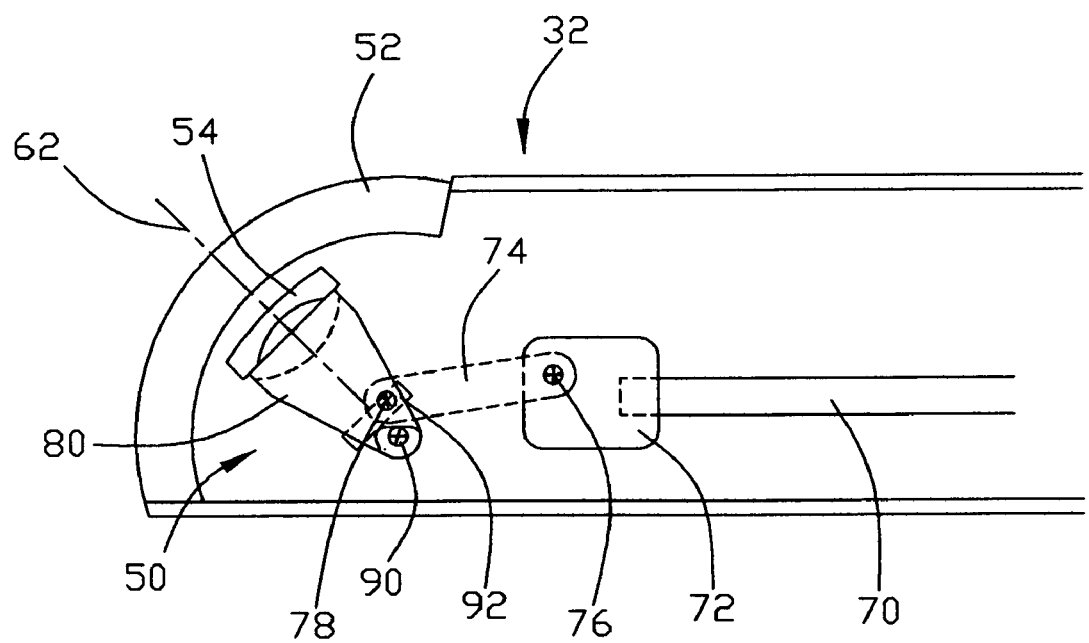
FIG. 6 is a sectional elevation view of the object input end of the arthroscope of FIG. 5, adjusted for a middle view, showing the input lens and CCD control, constructed in accordance with an embodiment of the present invention.

Referring now to FIGS. 5 and 6, in an alternative embodiment, a CCD 92 is mounted on input lens frame 80. CCD 92 has a receptor surface 92A. In contrast with the embodiment of FIGS. 3 and 4, mirror 56, mirror holder 86, prism 59, and focusing lens 60 have been eliminated. The placement of CCD 92 causes CCD 92 to substitute for some of those elements and reduces or eliminates the need for those elements. CCD receptor surface 92A is disposed in the focal plane of input lens 54. In this embodiment, input lens 54 is both an input and focusing lens for the image object captured by arthroscope 30. As input lens 54 and CCD receptor surface 92A are fixed in relation to each other such that their relative positions, including the distance and the angle between them, do not vary. When mounted on input lens frame 80, input lens 54 and CCD receptor surface 92A are movable and move as a unit. Input lens frame 80 rotates around axle 90 and rotates between a maximum upward view and a maximum downward view position, approximately corresponding to, and limited by, the field of view afforded by input window 52. The movement of input lens frame 80 allows the viewing position of arthroscope 30, and thus the particular input image captured in arthroscope 30, to be variable. Because input lens 54 and CCD 92 are both synchronously movable, a focused image is maintained on the CCD through the total viewing range defined by the maximum upward and maximum downward position.

In this embodiment, object rays pass through input window 52 and are refracted through input lens 54 and create an image plane on CCD receptor surface 92A. The image corresponding to the object rays is then relayed to control end 33. In the embodiment shown, the input lens frame 80 is fixed to a push rod yoke 72. The position of the input lens 54 is adjusted by the push rod 70 engaging the input lens frame 80 through an input lens connecting rod 74. The input lens connecting rod 74 is connected to the push rod 70 by yoke pin 76. Input lens connecting rod 74 is connected to the input lens frame 80 through an input lens frame pin 78. As the push rod 80 moves back and forth along the longitudinal axis of housing tube 31, the connecting rod 74 shifts the position of input lens frame 80 and of input lens 54.

The lighting assembly 42, as illustrated in FIG. 2, includes a light source 41 with an external optical fiber light guide to transmit light to the light relay assembly 43 that extends into arthroscope 30. Any conventional external light source and light guide may be used. Typically, external light source 41 is connected at an angle oblique to the axis of housing tube 31. Lighting assembly 42 may include a condenser lens to focus light from external source 41 onto the input end of the light relay assembly 43. Light relay assembly 43 may include one or more optical fiber bundles. In some embodiments, light relay assembly 43 is an optical fiber bundle that extends to input end 32 of arthroscope 30. In alternative embodiments, light relay assembly 43 may include structures other than optical fiber bundles.

CCD 61 converts the object image into a digital image that can be viewed, for example, on a TV or CRT screen. CCD 61 can be used to replace a field and relay system, or additional focusing lenses and mirrors, thereby decreasing the cost and complexity of a variable view arthroscope. Any suitable CCD can be used, with dimensions appropriate to fit in the tubular housing at the input end of an arthroscope. CCD 61 preferably has high resolution, and good color reception. In certain embodiments, CCD 61 is able to withstand autoclaving, a process used for sterilization of medical equipment. In certain embodiments, wires, not shown, convey the image from CCD 61 to outer control portion 35. In certain embodiments, a connector in outer control portion 35 transfers the signal to a signal processor cable. In alternate embodiments, wireless communication techniques may be used to convey data from CCD 61 to outer control portion 35 or to a suitable display device.

The language used herein is used for purposes of reference and not limitation. While the invention has been particularly shown and described with reference to preferred embodiments, it will be apparent to those skilled in the art that various modifications and alterations can be made in the device of the present invention without departing from the spirit and scope of the invention.

What is claimed is:

1. A variable view arthroscope with a plurality of viewing positions in a viewing range between a first end viewing position and a second end viewing position, comprising:
   a tubular housing having a longitudinal axis and an input end;
   an input lens in the input end of the housing, the input lens being rotatable around a first axis relative to the housing;
   a mirror in the input end of the housing, the mirror being rotatable around the first axis relative to the housing and wherein the input lens has a first angular change between a first viewing position and a second viewing position and the mirror has a second angular change between the first viewing position and the second viewing position, and the second angular change is half the first angular change; and
   a CCD in the housing, the CCD having a receptor surface;
   wherein an optical path is defined such that object rays received at the input end pass through the input lens, reflect from the mirror and impinge on the receptor surface, and wherein the movement of the input lens and the first mirror varies the view of the arthroscope.

2. The variable view arthroscope of claim 1, further comprising a prism disposed in the optical path between the mirror and the receptor surface.

3. The variable view arthroscope of claim 2, wherein the prism is fixed.

4. The variable view arthroscope of claim 1, further comprising a focusing lens disposed in the optical path between the mirror and the receptor surface.

5. The variable view arthroscope of claim 4, wherein the focusing lens and the CCD are arranged so that the object rays are focused from the focusing lens onto the receptor surface of the CCD.

6. The variable view arthroscope of claim 5, wherein the optical axis of the focusing lens is parallel to the longitudinal axis of the housing tube.

7. The variable view arthroscope of claim 4, further comprising a prism disposed in the optical path between the mirror and the receptor surface.

8. The variable view arthroscope of claim 7, wherein the prism and the focusing lens are arranged so that object rays reflect from the prism into the focusing lens.

9. The variable view arthroscope of claim 8, wherein the focusing lens is coaxial with the prism.

10. The variable view arthroscope of claim 1, wherein the length of a rim object ray from the input lens to the CCD is the same in the plurality of viewing positions.

11. The variable view arthroscope of claim 10, wherein the length of the two rim object rays from the input lens to the CCD is the same in the plurality of viewing positions.

12. The variable view arthroscope of claim 11, wherein the length of the two object rim rays are equal to each other in the plurality of viewing positions.

13. The variable view arthroscope of claim 1, wherein the first mirror is rotatable by approximately 30 degrees between the first end viewing position and the second end viewing position.

14. The variable view arthroscope of claim 1, wherein the middle viewing position in the viewing range is at an angle about 45 degrees from the longitudinal axis.

15. The variable view arthroscope of claim 1, wherein the viewing range is greater than 100 degrees.

16. A variable view arthroscope with a plurality of viewing positions in a viewing range between a first end viewing position and a second end viewing position, comprising:
   a tubular housing having a longitudinal axis and an input end;
   an input lens in the input end of the housing, the input lens having a focal plane, the input lens being rotatable relative to the housing;
   a CCD in the input end of the housing, the CCD having a receptor surface disposed in the focal plane of the input lens and being rotatable relative to the housing and wherein the input lens has a first angular change between a first viewing position and a second viewing position and the CCD has a second angular change between the first viewing position and the second viewing position, and the second angular change is half the first angular change; and
   wherein an optical path is defined such that object rays received at the input end pass through the input lens and impinge on the receptor surface, and wherein the movement of the input lens and the CCD varies the view of the arthroscope.

17. The variable view arthroscope of claim 16, wherein the distance and the angle between the input lens and the CCD do not vary when the view of the arthroscope is varied.

18. The variable view arthroscope of claim 16, wherein the input lens and the CCD are mounted on an input lens frame and the input lens frame pivots around a first axis to vary the view of the arthroscope.

19. The variable view arthroscope of claim 16, wherein the input lens has a first angular change between a first viewing position and a second viewing position and the CCD has a second angular change between the first viewing position and the second viewing position, and first angular.

* * * * *